Figure 1:
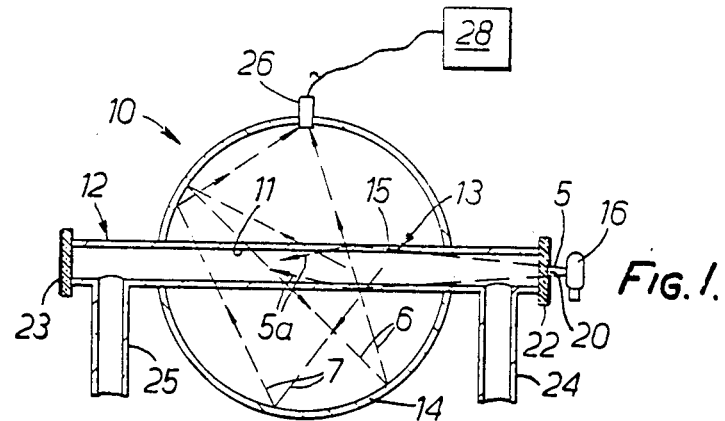

United States Patent [19]
Coogan

[11] Patent Number: 4,690,560
[45] Date of Patent: Sep. 1, 1987

[54] OPTICALLY BASED MEASUREMENT OF FLUID PARAMETERS

[75] Inventor: Clive K. Coogan, Canterbury, Australia

[73] Assignee: Commonwealth Scientific and Industrial Research Organization, Australia

[21] Appl. No.: 717,264

[22] PCT Filed: Jun. 29, 1984

[86] PCT No.: PCT/AU84/00122
§ 371 Date: Feb. 28, 1985
§ 102(e) Date: Feb. 28, 1985

[87] PCT Pub. No.: WO85/00426
PCT Pub. Date: Jan. 31, 1985

[30] Foreign Application Priority Data

Jun. 30, 1983 [AU] Australia .......... PG0051/83

[51] Int. Cl.$^4$ .......... G01N 21/49
[52] U.S. Cl. .......... 356/338; 356/236; 356/246
[58] Field of Search .......... 356/336, 337, 338, 339, 356/236, 246

[56] References Cited

U.S. PATENT DOCUMENTS 4,212,539  7/1980  Berber et al. .......... 356/339
4,320,978  3/1982  Sato .......... 356/440
4,488,814 12/1984  Johnson .......... 356/446

OTHER PUBLICATIONS

Fujiwara et al, Liquid Core Optical Fiber Total Reflection Cell as a Colorimetric Detector for Flow Injection Analysis, *Analytical Chemistry*, May 1985, pp. 1012-1016.

Lei et al, Determination of Phosphorus in Natural Waters by Long Capillary Cell Absorption Spectrometry, *Analytical Chemistry*, May 1983, pp. 951-955.

*Primary Examiner*—R. A. Rosenberger
*Attorney, Agent, or Firm*—Sughrue, Mion, Zinn, Macpeak and Seas

[57] ABSTRACT

Optical measurement apparatus includes a cell (12) adapted to receive fluid for testing and a light source (16) arranged to direct an incident light beam (5) into the cell. A hollow intergration sphere (14) and light-sensitive detector (26) are provided to detect at least a pre-determined portion of light emitted by a segment (13) of the cell transversely of the direction of said incident light beam.

The light source (16) and the cell (12) are arranged so that the light incident on the cell is not collimated but, as it traverses segment of the cell, is confined to the cell by total internal reflection, unless otherwise scattered by particles in the cell.

8 Claims, 3 Drawing Figures

OPTICALLY BASED MEASUREMENT OF FLUID PARAMETERS

This invention relates to the optically based measurement of fluid parameters and as such has application to any context in which a fluid, which may be a sample, emits light in random directions in response to a defined incident beam. The emitted light may indicate, e.g., a scattering or fluorescence effect.

A particular class of measurement of interest is nephelometry, in particular turbidimetry of liquids. In the classical nephelometer, a beam of incident light is passed through the test liquid so that some light is scattered by particles suspended in the liquid. The light which is not scattered, or is scattered through a very small angle only, continues on to a transmission photocell detector. The ratio of the detected to the incident intensity, taking into account the path length through the liquid, is considered to be a reliable measure of the turbidity of the liquid, especially for medium scattering power.

Where the test liquid is contained in a sample cell, it is known to employ an integration sphere to collect and measure the scattered light. This sphere was first used to collect a conical portion of the scattered light. In order to improve sensitivity at very low degrees of turbidity, it has been proposed, in U.S. Pat. No. 4,320,978 to Sato, to mount the sample cell as a straight transparent tube diametrically of, and substantially wholly within, the integration sphere. The incident light is a collimated beam of width matching the interior cross-section of the tubular cell and is fully absorbed after one traversal to ensure that the transmission light is not variably reflected or diffused back into the sample liquid.

The present invention stems from the realization that an especially simple and sensitive measuring instrument, having application as a nephelometer or fluorimeter, may be obtained by appreciating the utility of total internal reflection within a sample cell.

The invention accordingly affords optical measurement apparatus comprising:

a cell adapted to receive fluid for testing;

a light source arranged to direct an incident light beam into the cell; and means to detect at least a pre-determined portion of light emitted by a segment of the cell transversely of the direction of said incident light beam;

wherein the light source and the cell are arranged so that the light incident on the cell is not collimated but, as it traverses said segment of the cell, is confined to the cell by total internal reflection unless otherwise scattered by particles in the cell.

The segment of the cell may of course comprise the whole cell.

The apparatus may further include an aperture through which the incident light beam diverges into or towards the cell at an angle below the critical angle for total internal reflection in the cell.

Preferably, the incident light is arranged to traverse said segment of the cell more than once. This may be effected by configuring the sample cell as a helical tube or by placing reflectors at opposite ends of a straight elongate cell.

The detection means is advantageously a hollow integration sphere or ellipsoid enclosing said segment of the cell, and a light sensitive detector on or adjacent the inside surface of the sphere or ellipsoid.

The invention also provides a method for carrying out optically based measurement of a fluid parameter, comprising directing uncollimated incident light into a cell containing the fluid so that, as it traverses a segment of the cell, the light is confined to the cell by total internal reflection, unless otherwise scattered by particles in the cell, and detecting at least a pre-determined portion of light emitted by said segment of the cell.

Figure 2:
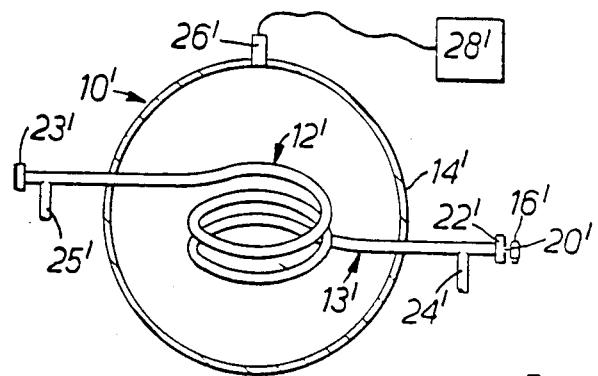
Figure 3:
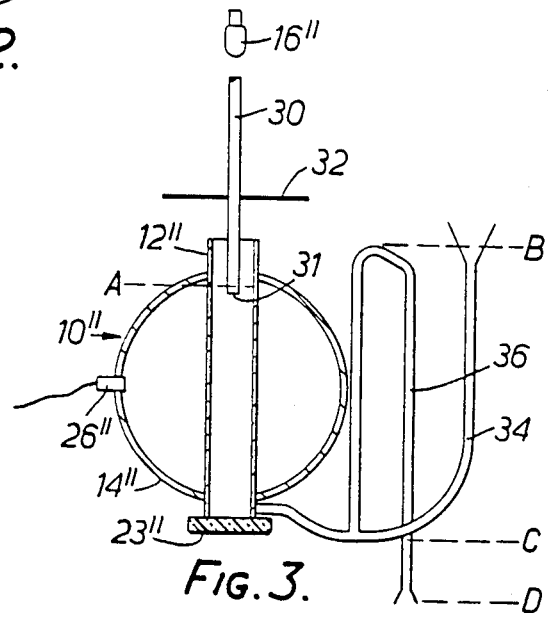

The invention will be further described, by way of example only, with reference to the accompanying drawings, in which FIGS. 1, 2 and 3 schematically depict, in partial cross-section, three alternative embodiments of apparatus in accordance with the invention, intended primarily for use as nephelometers. Like parts in the drawings are indicated by like reference numerals wherever appropriate.

The measurement apparatus 10 depicted in FIG. 1 includes an elongate, highly transparent tubular cell 12 extending through an integration sphere 14 so that the axis of the cell is coincident with a diameter of the sphere. Any convenient source of light 16 is arranged on the axis of cell 12 so as to direct an uncollimated beam 5 of incident light through an aperture 20 in the back-silvering of glass reflector 22 which closes off one end of the cell. The other end of the cell is closed by a second back-silvered glass reflector 23 which is similar to reflector 22 except that its silvering has no central aperture. Reflectors 22, 23 return light in the cell which reaches the ends of the cell.

Cell 12 is provided, adjacent its respective ends, with respective inlet and outlet ports 24, 25 by which fluid, typically liquid, may be admitted to and withdrawn from the cell.

Integration sphere 14 is an opaque light trap fitted with a photocell detector 26 at one point on its inner surface. Substantially all light emitted from the segment 13 of cell 12 within the sphere is eventually received at detector 26. Such spheres, which are designed to exhibit negligible or minimal absorption of the interior light, are considered to afford a reliable measure of the total intensity of light within their interior. Photocell 26 is electrically connected to a calibratable circuit 28 of conventional design for providing an output, preferably a read-out, indicative of the intensity of light at detector 26.

Source 16 and aperture 20 are arranged so that incident light admitted to cell 12 and subsequently transmitted and retransmitted, by reflection at reflectors 22, 23, within the cell will, unless otherwise scattered by particles in the liquid, be confined to the cell by virtue of total internal reflection from the glass-air interface 15 at the cylindrical outside surface of the cell. This effect, which is depicted for an incident light beam 5 at 5a in FIG. 1, will occur provided the maximum angle of the light admitted at aperture 20 with respect to the internal surface of the cell is clearly less than the critical angle at the glass-air interface, making due allowance for refraction at the inside liquid glass interface 11. With many liquids having refractive indices similar to glass, little or no such allowance may be necessary but this may not be the case with low refractive index fluids such as gases. Provided the unscattered light is confined in this manner at least to segment 13 of the cell, the only light which will escape to the interior of integration sphere 14, and then to detector 26, will be, with appropriate choice of wavelength, light scattered from particles in the liquid. Such light is exemplified by rays 6, 7 in FIG. 1.

Because the whole of the scattered light over a substantial portion of cell 12 is collected, the measured intensity at detector 26 is considered to be a highly reliable measure of the turbidity, i.e. of the density of particles in the liquid. Moreover, because there is spherical 360° collection of scattered light, the instrument remains highly sensitive even at very low turbidities. Circuit 28 may be calibrated, and so provide a direct indication of turbidity, by reference to a standard turbidity liquid such as Formazin.

In the arrangement depicted in FIG. 1, light from source 16 is so baffled by aperture 20 that the only light to enter the cell is light at such angle to the cylindrical wall of the cell as to be totally internally reflected. Alternatively, the length of the cell outside integrating sphere 14 might be so arranged that any of the light which enters the cell at too great an angle with the cell wall for total internal reflectance shall have penetrated the wall before it reaches cell segment 13 within the integrating sphere. There are other methods of securing the same effect, for example the transmission of the incident light along a light pipe of the same refractive index as the glass walls of the cell.

It will be well understood that cell 12 should be free of flaws such as bubbles, occlusions and inhomogeneity of refractive index, since these flaws will themselves cause scattering of light traversing the cell.

FIG. 2 depicts an alternative embodiment of apparatus 10' in which multiple traversals by the unscattered incident light with respect to sphere 14' are obtained by forming the cell as a helical tube 12' within the sphere.

The sensitivity of either embodiment may be enhanced by employing as the light source 16, a gas laser or a solid state diode laser to greatly increase the light source strength, and/or by chopping the incident light so that the signal to noise ratio can be increased by the use of phase sensitive detection which discriminates against the noise. Such chopping can be effected electrically if a laser diode or LED is used or mechanically in the case of a gas laser or gaseous discharge tube.

It will be appreciated from the above discussion that the illustrated apparatus, and the method embodied therein, may be employed for purposes other than nephelometry. For example, with suitable ancillary equipment, the arrangement is capable of optimizing the measurement of fluorescence. In this application, the exciting, e.g. ultra-violet, light is confined to the tubular cell, but light emitted at an angle to the cell wall greater than the critical angle for total internal reflection at the outer interface will escape. The embodiment of FIG. 2 is especially useful for fluorescence applications.

In an industrial application, an apparatus such as that of FIGS. 1 and 2 may be an in situ unit through which a liquid of a monitored process is continuously circulated and a parameter, e.g. the turbidity continuously observed. Alternatively, the apparatus may be employed as a sample analyser and it may then be convenient to automate the circulation of successive samples through the cell. This might be done in a number of known ways, for example by transporting the samples as discrete packets of liquid separated by air bubbles or separated by another immiscible fluid such as paraffin. Each sample can be followed by a distilled water sample to clear the cell of contamination: in this connection, provision, such as detachable ends or an adjacent ultrasonic cleaner, might be made for regular thorough cleansing of the interior of the cell.

If the samples are circulated as discrete packets of liquid separated by air bubbles, it would be preferable to incline the axis of the sample cell as a precaution against "bubble locking", as bubbles are excellent scatterers of light and would give misleading results. An alternative sample circulation technique would rely on the autosyphon principle. In one such configuration, the tubular cell is inclined and filled from the bottom to a critical overflow level at which automatic draining occurs.

A third embodiment 10" of apparatus according to the invention utilizing the autosyphon principle is depicted in FIG. 3. In this case, the tubular cell 12" is arranged with its axis vertical on a base comprising a back-silvered glass reflector 23". Incident light is introduced from above along a glass rod 30 which passes through a black baffle 32 above the open top of cell 12". Liquid sample is introduced into a tube 34, at a level B just below the top of the cell, for admission to the bottom of the cell. An inverted U-autosyphon tube 36 branches from tube 34 at a level C below the bottom of cell 12", turns at level B, and opens at level D below C.

Liquid is pumped in along tube 34 to the level A, just covering the end 31 of glass rod 30. This introduces the advantage that the incident light interface into the liquid is always optically flat and invariant in terms of surface tension and the like. Level A is maintained until the measurement is made and pumping is then recommenced. At level B, autosyphon overflow occurs, draining both the cell 12" and the supply tube 34.

This third embodiment simplifies cleaning as the glass rod is removable and can be replaced in exactly the same position by kinematic seating and the remainder of the instrument can be cleaned by "pipe cleaner" techniques. The glass rod 30, which acts as a light pipe, is preferably of the same refractive index as the tubular cell 12", so that it sheds all the rays of incident light outside the critical angle for total internal reflection. Baffle 32 prevents this light from entering the liquid and thus escaping through the cell walls. The final few millimeters of rod 30 may be advantageously silvered and the silvering covered by inert polymer to prevent variations due to level differences or meniscus difference from run to run, although the front face 31 of the rod in the liquid is kept clear of silver or polymer.

By relying upon total internal reflection rather than collimation of the incident light, the described embodiments disperse with the requirement, for example in the device of U.S. Pat. No. 4,320,978 to Sato, for additional optics and for precision in the relative disposition of the components. Moreover, both total internal relection and multiple traversal allows advantageous increases in path length and therefore in the sensitivity of measurement. Relying on total internal reflection of uncollimated light permits use, in particular, of a helical tube to obtain multiple traversals within the integration sphere—an option not possible with collimated light.

I claim:

1. Optical measurement apparatus comprising:
   an elongate tubular sample cell (12) adapted to receive fluid for testing;
   a light source (16) arranged to direct an incident light beam into the cell; and
   hollow light integration means (14', 26') about said cell to detect at least a pre-determined portion of light emitted by the cell transversely of the direction of said incident light beam, said cell being transparent to such emitted light;

wherein the light source and the cell are arranged so that said incident light beam is not collimated but, as it traverses said cell, is confined to the cell by total internal reflection, unless otherwise scattered by particles in the cell;

and wherein said tubular sample cell is coiled within said light integration means so as to substantially increase the path length of the incident light beam within the light integration means.

2. Optical measurement apparatus according to claim 1, further comprising an aperture (20) through which the incident light beam diverges into or towards the cell at an angle below the critical angle for total internal reflection in the cell.

3. Optical measurement apparatus according to claim 1, further comprising a calibratable circuit (28) arranged to provide an output indication of the intensity of said portion of light emitted by the cell.

4. Optical measurement apparatus according to claim 1, further comprising reflectors (22', 23') at opposite ends of said cell.

5. Optical measurement apparatus according to claim 1, wherein said cell is of helical configuration.

6. Optical measurement apparatus according to claim 1, wherein said light integration means comprises a hollow integration sphere (14') or ellipsoid said segment of the cell, and a light sensitive detector (26') on or adjacent the inside surface of the sphere or ellipsoid.

7. Optical measurement apparatus according to claim 6, wherein said light integration means comprises a hollow integration sphere, the axis of the tubular cell being substantially co-incident with a diameter of the sphere.

8. Optical measurement apparatus according to claim 1, wherein said cell includes fluid inlet and outlet ports (24', 25") spaced apart in the general direction in which said incident light beam traverses the cell.

* * * * *